United States Patent [19]
Silvestrini

[11] Patent Number: 5,766,171
[45] Date of Patent: Jun. 16, 1998

[54] ELECTROSURGICAL PROCEDURE FOR THE TREATMENT OF THE CORNEA

[75] Inventor: Thomas A. Silvestrini, Alamo, Calif.

[73] Assignee: KeraVision, Inc., Fremont, Calif.

[21] Appl. No.: 629,062

[22] Filed: Apr. 8, 1996

Related U.S. Application Data

[63] Continuation of Ser. No. 194,207, Feb. 9, 1994, abandoned.

[51] Int. Cl.$^6$ ............................................. A61B 17/36
[52] U.S. Cl. .................. 606/49; 606/33; 606/41; 606/50
[58] Field of Search ...................... 606/5, 32-52

[56] References Cited

U.S. PATENT DOCUMENTS

| | | | |
|---|---|---|---|
| 3,970,088 | 7/1976 | Morrison | 606/48 |
| 4,033,351 | 7/1977 | Hetzel . | |
| 4,060,087 | 11/1977 | Hiltebrandt et al. | 606/48 |
| 4,202,337 | 5/1980 | Hren et al. . | |
| 4,228,800 | 10/1980 | Degler, Jr. et al. . | |
| 4,326,529 | 4/1982 | Doss et al. | 606/41 |
| 4,367,744 | 1/1983 | Sole . | |

(List continued on next page.)

FOREIGN PATENT DOCUMENTS

| | | |
|---|---|---|
| WO 92/21278 | 12/1992 | WIPO . |
| WO 92/21285 | 12/1992 | WIPO . |
| WO 93/08755 | 5/1993 | WIPO . |
| WO 93/08756 | 5/1993 | WIPO . |
| WO 93/08757 | 5/1993 | WIPO . |
| WO 93/08869 | 5/1993 | WIPO . |
| WO 93/20767 | 10/1993 | WIPO . |
| WO 93/20768 | 10/1993 | WIPO . |
| WO 93/20770 | 10/1993 | WIPO . |
| WO 93/20877 | 10/1993 | WIPO . |
| WO 93/20878 | 10/1993 | WIPO . |
| WO 93/20886 | 10/1993 | WIPO . |
| WO 93/20893 | 10/1993 | WIPO . |
| WO 93/20894 | 10/1993 | WIPO . |

OTHER PUBLICATIONS

"Radial Thermokeratoplasty for Hyperopia" by McDonnell; Refractive & Corneal Surgery; vol 5; Jan./Feb. 1989 pp. 50–54.

"Lamellar Corneal Stromectomy" by Krwawicz; received in PTO Sep. 19086 pp. 828–833.

Singer, "Advances in Radio Therapy for Hyperopia Decrease Regression, a Problem in the Past," *Ocular Surgery News*, pp.30–31 (Sep. 15, 1997).

Dialog™ Computer Database abstract of Osterweil, N., ed., "Cornea appears to tolerate inlay ring" *Ophthalmology Times* (Jul. 1, 1991) p. 1.

*Primary Examiner*—David M. Shay
*Attorney, Agent, or Firm*—Morrison & Foerster LLP

[57] ABSTRACT

This invention is a device and procedure for the correction of optical abnormalities in a human eye. It involves use of an inventive electrosurgical energy probe with specific physical configurations. The process preferably utilizes a high frequency RF electro-desiccation or ablation device. The procedure involves the initial step of forming at least one access site allowing access to the corneal volume behind the Bowman's Layer. It preferably is placed in the anterior surface of the cornea through and ending posterior to the Bowman's layer of the eye. The electrosurgical probe is then introduced into the access site and, depending upon the visual abnormality to be corrected, the probe is activated to adjust the volume of the corneal stromal layers through ablation or desiccation. The shape of the volume desiccated or ablated is dependent upon the aberration to be corrected. For instance, if the optical aberration to be alleviated is hyperopia, a circular corneal volume reduction taking place about the outer periphery of the corneal mass may be accomplished. In other instances, such as for the treatment of astigmatism, certain smaller sections of the corneal volume may be shrunk. In certain circumstances, Bowman's layer may be cut to allow the curvature of the cornea to change after the corneal volume adjustment. These relief cuts may be radial, circular, semicircular or any other form appropriate for the option adjustment needed.

36 Claims, 9 Drawing Sheets

U.S. PATENT DOCUMENTS

| | | | |
|---|---|---|---|
| 4,381,007 | 4/1983 | Doss | 606/27 |
| 4,438,766 | 3/1984 | Bowers . | |
| 4,452,235 | 6/1984 | Reynolds . | |
| 4,481,948 | 11/1984 | Sole . | |
| 4,559,943 | 12/1985 | Bowers . | |
| 4,671,276 | 6/1987 | Reynolds . | |
| 4,688,570 | 8/1987 | Kramer et al. . | |
| 4,766,895 | 8/1988 | Reynolds . | |
| 4,799,478 | 1/1989 | Federov et al. . | |
| 4,805,616 | 2/1989 | Pao . | |
| 4,807,623 | 2/1989 | Lieberman | 606/166 |
| 4,815,463 | 3/1989 | Hanna . | |
| 4,901,719 | 2/1990 | Trencowsky et al. . | |
| 4,907,587 | 3/1990 | Fedorov et al. . | |
| 4,941,093 | 7/1990 | Marshall et al. . | |
| 4,961,744 | 10/1990 | Kilmer et al. . | |
| 5,009,656 | 4/1991 | Reimels | 606/50 |
| 5,025,811 | 6/1991 | Dobrogowski et al. . | |
| 5,174,304 | 12/1992 | Latina et al. . | |
| 5,201,730 | 4/1993 | Easley et al. . | |
| 5,203,353 | 4/1993 | Easley et al. . | |
| 5,215,104 | 6/1993 | Steinert . | |
| 5,257,451 | 11/1993 | Edwards et al. . | |
| 5,263,951 | 11/1993 | Spears et al. . | |
| 5,346,491 | 9/1994 | Oertli . | |
| 5,533,999 | 7/1996 | Hood et al. | 606/5 |

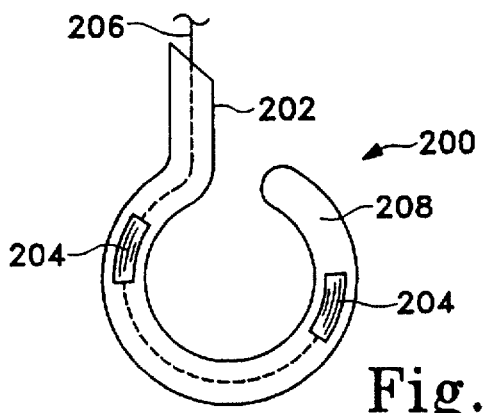
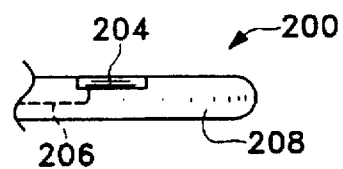
Fig. 5A  Fig. 5B
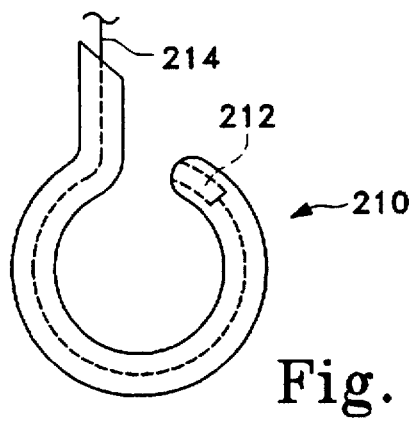
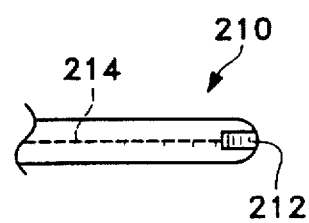
Fig. 6A  Fig. 6B
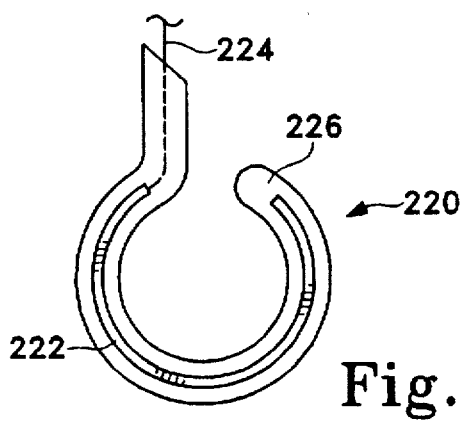
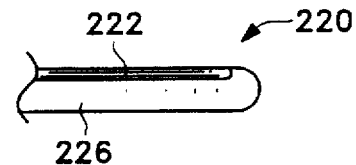
Fig. 7A  Fig. 7B
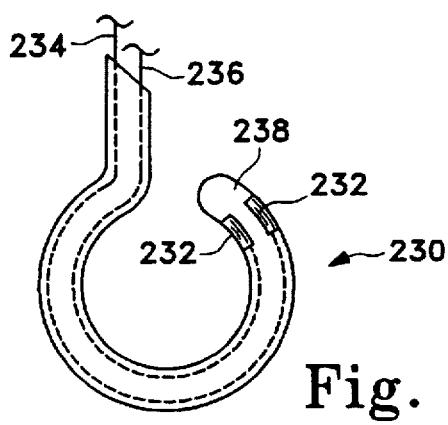
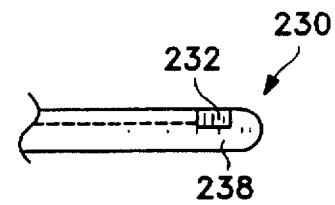
Fig. 8A  Fig. 8B

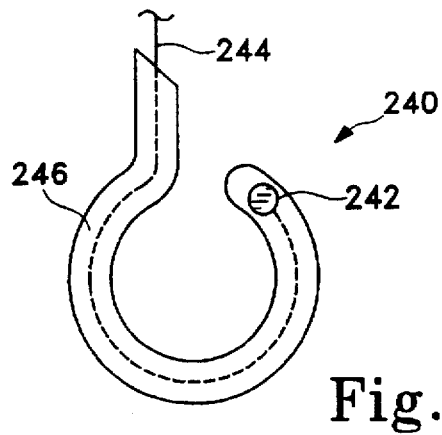 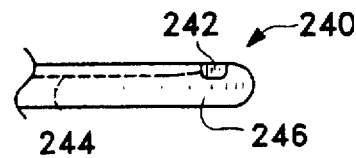
Fig. 9A    Fig. 9B
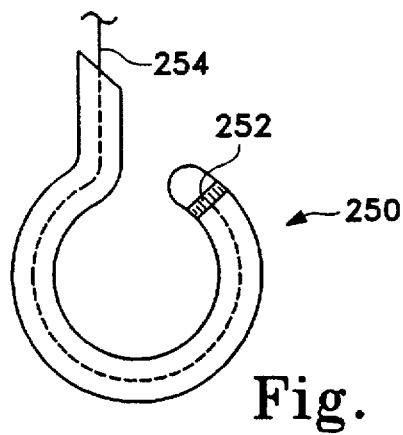 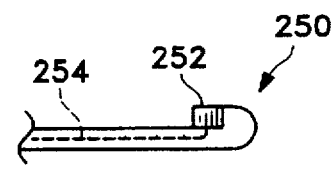
Fig. 10A    Fig. 10B
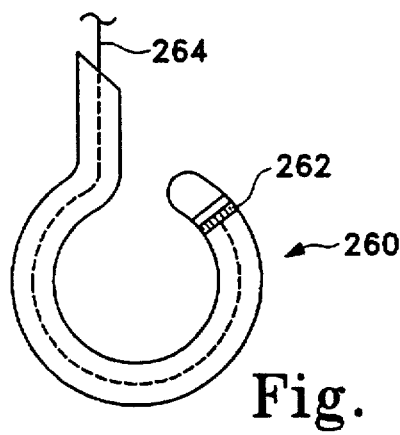 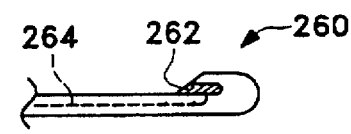
Fig. 11A    Fig. 11B

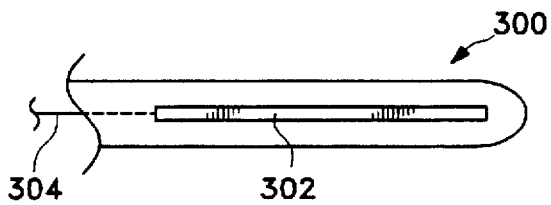 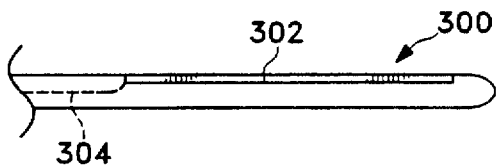
Fig. 12A  Fig. 12B
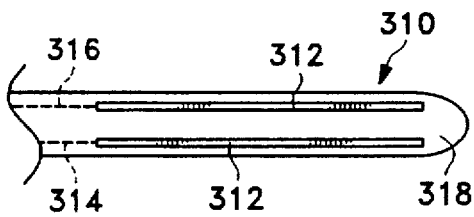 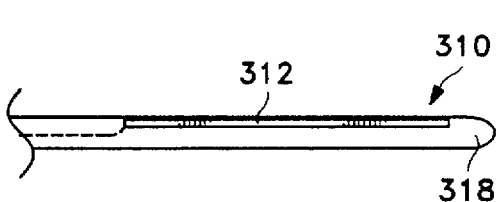
Fig. 13A  Fig. 13B
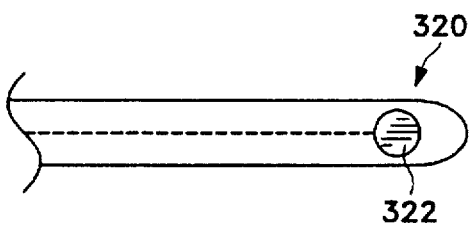 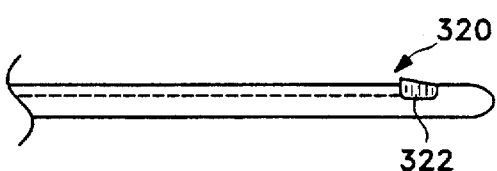
Fig. 14A  Fig. 14B
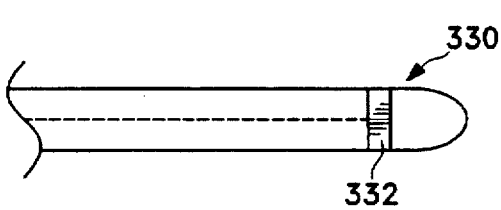 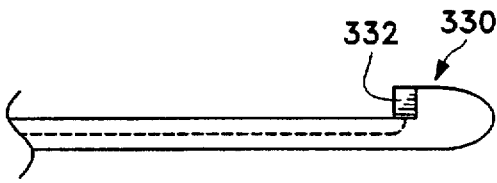
Fig. 15A  Fig. 15B

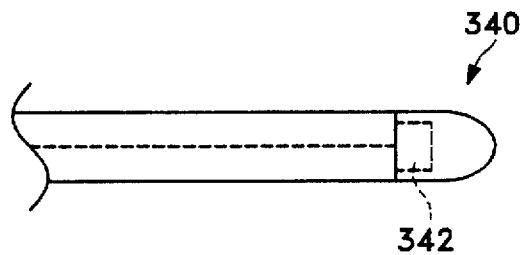
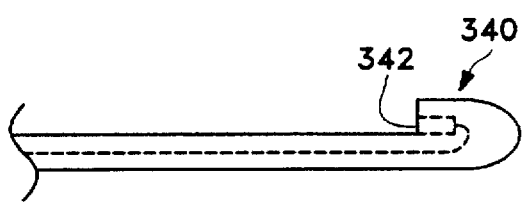
Fig. 16A  Fig. 16B
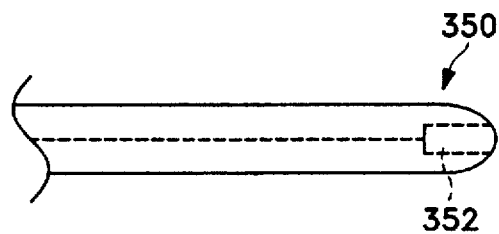
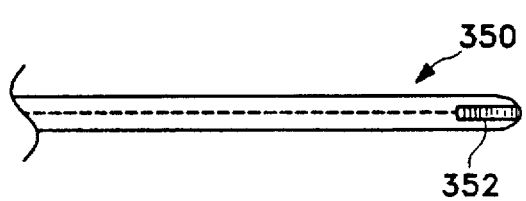
Fig. 17A  Fig. 17B
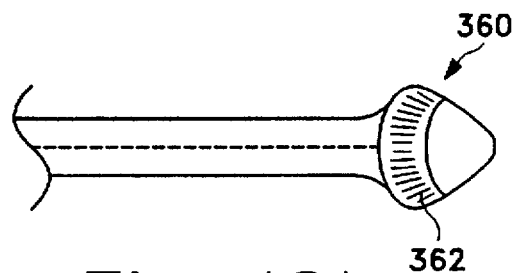
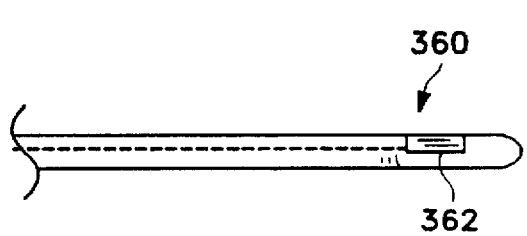
Fig. 18A  Fig. 18B
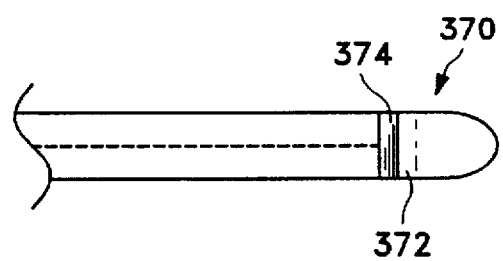
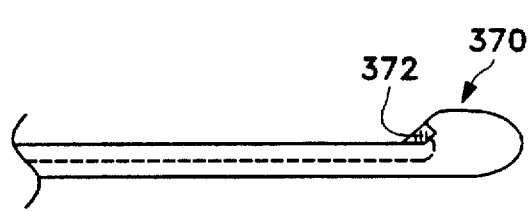
Fig. 19A  Fig. 19B

ELECTROSURGICAL PROCEDURE FOR THE TREATMENT OF THE CORNEA

This application is a File Wrapper Continuation of application Ser. No. 08/194,207, filed Feb. 9, 1994, now abandoned.

FIELD OF THE INVENTION

This invention is a procedure for the correction of optical abnormalities in a human eye. It involves use of an electrosurgical energy probe which may be of a specific physical configuration as outlined below. This invention also includes suitable electrodes for performing the noted process. The process preferably utilizes a high frequency RF electrodesiccation or ablation device. The procedure involves the initial step of forming at least one access site allowing access to the corneal volume behind the Bowman's layer. It (the access site) preferably is placed in the anterior surface of the cornea through and ending posterior to the Bowman's layer of the eye. The electrosurgical probe is then introduced into the access site and, depending upon the visual abnormality to be corrected, the probe is activated to adjust the volume of the corneal stromal layers through ablation or desiccation. The shape of the volume desiccated or ablated is dependent upon the aberration to be corrected. For instance, if the optical aberration to be alleviated is hyperopia, a circular corneal volume reduction taking place about the outer periphery of the corneal mass may be accomplished. In other instances, such as for the treatment of astigmatism, certain smaller sections of the peripheral corneal volume may be shrunk. In certain circumstances, Bowman's layer may be cut to allow the curvature of the cornea to change after the corneal volume adjustment. These relief cuts may be radial, circular, semicircular or any other form appropriate for the optical adjustment needed.

BACKGROUND OF THE INVENTION

Anomalies in the overall shape of the eye can cause visual disorders. Hyperopia ("farsightedness") occurs when the front-to-back distance in the eyeball is too short. In such a case, parallel rays originating greater than 20 feet from the eye focus behind the retina. In contrast, when the front-to-back distance of eyeball is too long, myopia ("nearsightedness") occurs and the focus of parallel rays entering the eye occurs in front of the retina. Astigmatism is a condition which occurs when the parallel rays of light do not focus to a single point within the eye, but rather have a variable focus due to the fact that the cornea refracts light in a different meridian at different distances. Some degree of astigmatism is normal, but where it is pronounced, the astigmatism must be corrected.

Hyperopia, myopia, and astigmatism are usually corrected by glasses or contact lenses.

Another method for correcting those disorders is through the implantation of polymeric rings (intrastromal corneal rings or "ICR's") in the eye's corneal stroma to change the curvature of the cornea. Previous work involving the implantation of polymethylmethacrylate (PMMA) rings, allograft corneal tissue, and hydrogels is well documented. One of the ring devices involves a split ring design which is inserted into a channel previously dissected in the stromal layer of the cornea. A minimally invasive incision is used both for producing the channel and for inserting the implant. See, for instance, the use of PMMA intrastromal rings in U.S. Pat. Nos. 4,452,235 to Reynolds; 4,671,276 to Reynolds; 4,766,895 to Reynolds; and 4,961,744 to Kilmer et al.

Surgical methods for the correction of such disorders are known. Such methods include radial keratotomy (see, e.g., U.S. Pat. Nos. 4,815,463 and 4,688,570) and laser corneal ablation (see, e.g., U.S. Pat. No. 4,941,093).

There are other procedures for reshaping the surface of the cornea. Some involve surgery; others do not. Two patents dealing with the nonsurgical reshaping of the cornea are U.S. Pat. Nos. 4,326,529 to Doss, et al. and 4,381,007 to Doss. Both of these patents deal with the use of radio frequency energy to reshape the cornea of an eye. These involve the use of RF probes which are introduced noninvasively onto the cornea. They each involve an RF generating source which is placed on the anterior surface of the cornea and utilize saline solution to cool the corneal surface as the radio frequency current enters the eye. The RF apparently heats various stroma within the cornea and thereby reshapes the cornea as a biological response to the heat produced by the RF.

Other invasive ophthalmic surgical devices include U.S. Pat. No. 4,805,616, to Pao, which patent describes a bipolar probe device may be used in ophthalmic surgery. The device is only described in the performance of anterior capsulotomies. In that procedure, a limbal incision is made and the active probe tip is inserted between the anterior capsule of the eye's lens and the corneal endothelium. The anterior capsule is sequentially coagulated, becomes extremely friable, and then is removed by mechanical penetration with an additional mechanical device. No mention of treatment of a cornea is found.

Similarly, two patents to Easley et al., U.S. Pat. Nos. 5,201,730 and 5,203,353, show devices for penetrating and working in the vitreous humor of an eye using combination stripping tools and aspirators. The disclosed instrument may also have a bipolar diathermy device with an exterior needle surrounding and coaxial to a fiberoptic member. The diathermy device is used only to coagulate bleeding vessels found on the retinal surface or beneath preretinal membranes. No mention of treating the cornea is mentioned.

Two related applications, U.S. Pat. Nos. 5,025,811 to Dobrogowski et al., and 5,174,304, to Latina et al., show noninvasive methods for focal transcleral destruction of living human eye tissue. In general, these devices and their underlying procedures involve the use of electric currents for ablating eye tissue, particularly the ciliary process. Again, no mention of cornea treatment is seen.

This invention involves the introduction of an electrosurgical probe into the layers of the cornea to modify local sections of that corneal mass.

There are a variety of electrosurgical devices known. For instance, Hetzel, U.S. Pat. No. 4,033,351, shows a bipolar cutting electrode for high frequency surgery. The electrode shows what is said to be an improved electrode design having a number of metal tips.

U.S. Pat. No. 4,202,337, to Hren et al., shows a similar electrosurgical device for cutting or coagulation. It has a nonconductive handle with a blade assembly having a number of electrodes and an insulation member separating the various electrodes.

A similar and related patent to Degler Jr. et al., U.S. Pat. No. 4,228,800, shows an electrosurgical knife in which the blade assembly has a center electrode of specified thickness, insulation members secured to the center electrode, and a number of side electrodes secured to the insulation members. None of these devices discuss practice of a surgical procedure upon the posterior regions of a cornea.

U.S. Pat. No. 4,799,478, to Fedorov et al. teaches a device for the coagulation of biological tissues, preferably corneal tissue. The device disclosed by Fedorov et al. appears to be merely a heating device with a manner of carefully controlling the depth to which the heater or coagulator is introduced. The device is said to be useful for coagulation of biological tissue and the concept of changing "the curvature" of "eye tissues, e.g., cornea" is noted. The patent mentions the need for high accuracy to reach the goal of "to carry out coagulation of the eye cornea to a specific depth." Although it is not clear what result Fedorov et al. wishes to obtain in this first patent, Fedorov et al. in U.S. Pat. No. 4,907,587, mentions the use of thermal coagulation of the cornea along certain corneal surfaces to correct various optical aberrations in the eye. It should be noted that neither of these patents suggests the use of ablation or desiccation from the reverse side of the Bowman's layer to effect any change in the anterior corneal surface.

SUMMARY OF THE INVENTION

This invention is a method of altering the shape of the cornea, often, the anterior surface curvature of the cornea. The invention also includes certain electrosurgical probe configurations useful in this process. The procedure, in its preferred variations, does not entail significant surgical modification of the anterior corneal surface or of the Bowman's layer of the eye, except, in certain situations, adding surface incisions to act either as a stress relief function or to provide access for the electrosurgical probe.

An electrosurgical probe is a significant portion of this invention. It is used, preferably in desiccation or ablation mode, to change the volume of the mass of the cornea posterior to the Bowman's layer and found in the stromal regions of the cornea. By selectively modifying the volume of these regions, small amounts of the cornea may be controllably removed or shrunk and, upon removal of the electrosurgical probe from the cornea, the curvature of the anterior surface of the cornea will have changed and the refractive path of light entering the eye will be changed. As noted above, surface incisions may later be added to permit the anterior of the cornea, in particular, Bowman's layer, to conform to the underlying corneal tissue removal (volume change), thereby allowing for change in anterior corneal curvature.

The inventive procedure may be used for the treatment of hyperopia (farsightedness) or myopia. In this procedure, a small incision or access site may be made in the anterior surface of the cornea, which incision extends down through the Bowman's layer or through the sclera and into the intrastromal volume of the cornea. An electrosurgical probe, may be introduced through the incision and guided around within the corneal stroma from the outer periphery of the cornea. Activation of the electrosurgical probe in an ablation mode will cause vaporization of the regions of the cornea adjacent to the active areas of the probe. Activating the probe in a desiccation mode will shrink or necrose the region of the cornea adjacent to the active areas of the probe. After an appropriate necrosis, removal or shrinking of material is accomplished, the probe is removed and the anterior surface then relaxes to conform to the collapse or shrinkage of tissue formed by electrosurgical treatment of the corneal stromal tissue. In some instances, a modest incision in the anterior of the cornea may be desirable to allow curvature relaxation of the corneal anterior surface.

Another preferred procedure includes the alleviation of astigmatism by similar procedure. Small partial depth incisions may be made into the anterior surface of the cornea through Bowman's layer or through the sclera adjacent to the cornea to get under Bowman's layer, but not reaching so far as the posterior corneal surface or the anterior chamber. In a general sense, these initial incisions are made in the regions of the cornea or sclera to allow the electrosurgical probe to reach the corneal mass below the anterior surface which must be reduced to produce a symmetric corneal surface. In any event, an electrosurgical probe is then introduced through the incisions and a selected amount of material is removed or desiccated to alleviate the nonregularity of the corneal anterior surface.

Also as a part of this invention are certain monopolar, bipolar, and sesquipolar electrosurgical probe designs which are especially suitable for producing the specific tissue removal patterns desired in this procedure.

BRIEF DESCRIPTION OF THE DRAWINGS

FIGS. 5–11 A and B show top and side views of inventive circular RF electrosurgical probes.

FIGS. 12–19 A and B show top and side views of inventive straight RF electrosurgical probes.

DESCRIPTION OF THE INVENTION

Prior to explaining the details of the inventive procedures and devices, a short explanation of the physiology of the eye is needed.

Figure 1:
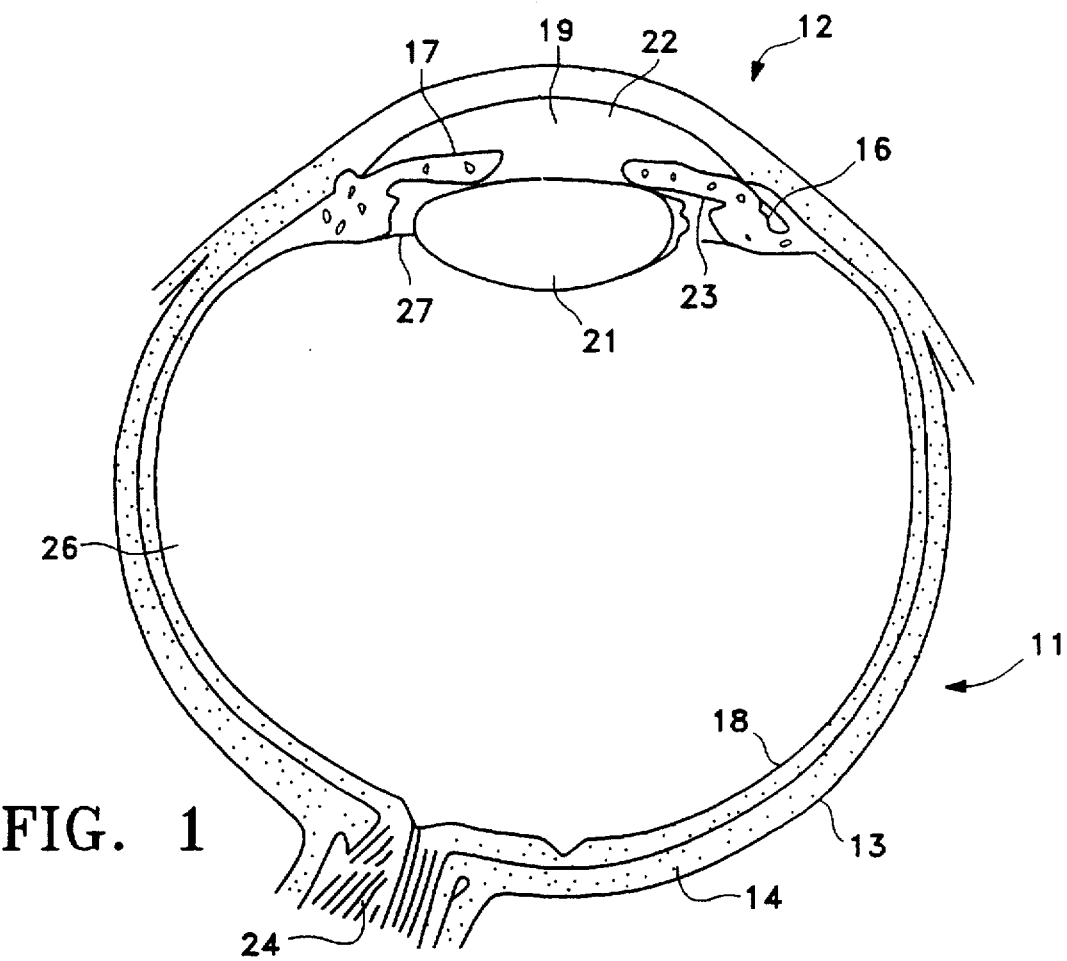
FIG. 1 is a schematic illustration of a horizontal section of the eye.

FIG. 1 shows a horizontal cross-section of the eye with the globe (11) of the eye resembling a sphere with an anterior bulged spherical portion representing the cornea (12).

The globe (11) of the eye consists of three concentric coverings enclosing the various transparent media through which the light must pass before reaching the light-sensitive retina (18). The outermost covering is a fibrous protective portion the posterior five-sixths of which is white and opaque and called the sclera (13), and sometimes referred to as the white of the eye where visible to the front. The anterior one-sixth of this outer layer is the transparent cornea (12).

A middle covering is mainly vascular and nutritive in function and is made up of the choroid, ciliary body (16), and iris (17). The choroid generally functions to maintain the retina (18). The ciliary body (16) is involved in suspending the lens (21) and accommodation of the lens. The iris (17) is the most anterior portion of the middle covering of the eye and is arranged in a frontal plane. It is a thin circular disc similar in function to the diaphragm of a camera, and is perforate near its center by a circular aperture called the pupil (19). The size of the pupil varies to regulate the amount of light which reaches the retina (18). It contracts also to accommodation, which serves to sharpen the focus by diminishing spherical aberration. The iris divides the space between the cornea (12) and the lens (21) into an anterior chamber (22) and the posterior chamber (23). The innermost portion of covering is the retina (18), consisting of nerve elements which form the true receptive portion for visual impressions.

The retina (18) is a part of the brain arising as an outgrowth from the fore-brain, with the optic nerve (24) serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body (26) is a transparent gelatinous mass which fills the posterior four-fifths of the globe (11). At its sides it supports the ciliary body (16) and the retina (18). A frontal saucer-shaped depression houses the lens.

The lens (21) of the eye is a transparent biconvex body of crystalline appearance placed between the iris (17) and vitreous body (26). Its axial diameter varies markedly with accommodation. A ciliary zonule (27), consisting of transparent fibers passing between the ciliary body (16) and lens (21) serves to hold the lens (21) in position and enables the ciliary muscle to act on it.

Referring again to the cornea (12), this outermost fibrous transparent coating resembles a watch glass. Its curvature is somewhat greater than the rest of the globe and is ideally spherical in nature. However, often it is more curved in one meridian than another giving rise to astigmatism. Most of the refraction of the eye takes place through the cornea.

Figure 2:
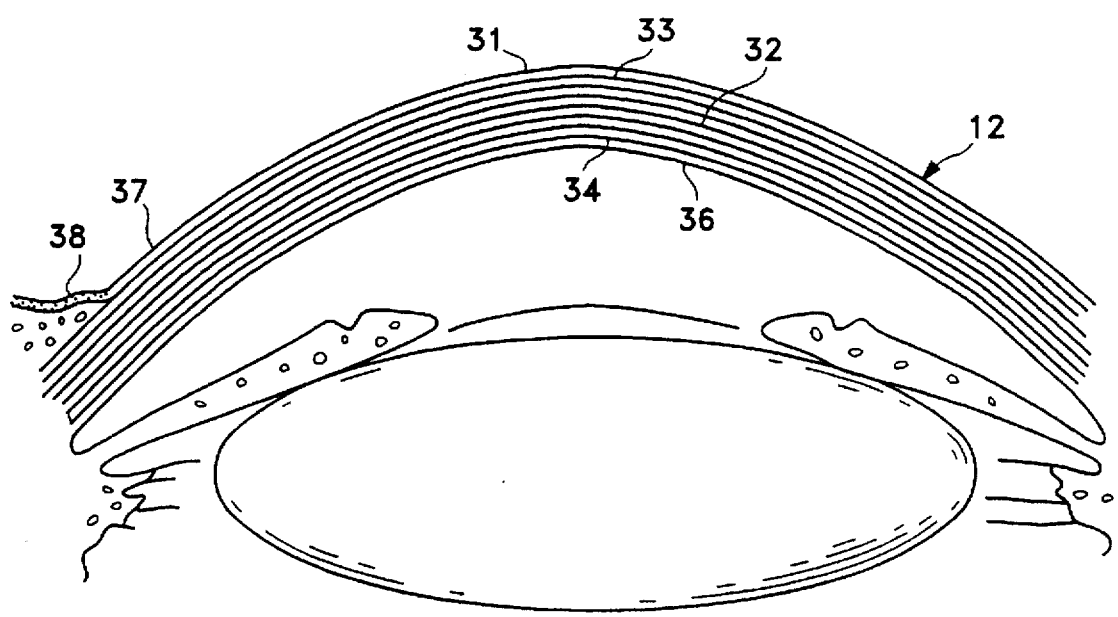
FIG. 2 is a schematic illustration of the anterior portion of the eye, showing various layers of the cornea.

FIG. 2 is a more detailed drawing of the anterior portion of the globe showing the various layers of the cornea (12) making up the epithelium (31).

An anterior limiting lamella (33), referred to as Bowman's membrane or layer, is positioned between the epithelium (31) and the stroma (32) of the cornea. When I refer to the "corneal mass," I mean the various stroma (32) between the Bowman's layer (33) and the Descemet's membrane (34). The corneal stroma (32) are made up of lamellae having bands of fibrils parallel to each other and crossing the whole of the cornea. While most of the fibrous bands are parallel to the surface, some are oblique, especially anteriorly. A posterior limiting lamella (34) is referred to as Descemet's membrane. It is a strong membrane sharply defined from the stroma (32) and resistant to pathological processes of the cornea.

The endothelium (36) is the most posterior layer of the cornea and consists of a single layer of cells and function to maintain transparency of the cornea (12). These epithelial cells are rich in glycogen, enzymes and acetylcholine and their activity regulates the transport of water and electrolytes through the lamellae of the cornea (12). The limbus (37) is the transition zone between the conjunctiva (38) and sclera on the one hand and the cornea (12) on the other.

There are a variety of different electrical surgical delivery probes which would be suitable in this invention. In general, there are two distinct electrosurgical delivery probe types: the monopolar probe and the bipolar probe. An in-between electrosurgical configuration applicable to this invention also exists and is known as sesquipolar. In each instance, some section of the human body is used to complete a circuit between one pole and the other. In the monopolar probe device, there is a single active contact which is inserted or otherwise contacted with the human body and it is the site at which some body activity, e.g., desiccation, ablation, necrosis, fulguration, or the like, takes place. To complete the circuit in a monopolar device, there must be another contact which is inactive and placed against the body in a location from the active contact. By "inactive" is meant that only an insignificant temperature rise occurs at that contact point. One such method of insuring that the inactive electrode is in fact "inactive" is to make it quite large in area. This causes the current to spread over a large area for completion of the circuit.

A bipolar electrode typically has two equal area active electrodes contained in the same electrode probe-handle structure. This symmetric bipolar electrode design produces a significant temperature rise at both electrodes.

In a monopolar or sesquipolar configuration, only one electrode has an area of tissue contact producing significant temperature rise. Unlike the monopolar configuration, however, the sesquipolar return electrode is not so remote, and thereby limits current flow through the body to the nearby return electrode. The return electrode area in the sesquipolar configuration electrode is usually at least three times the area of the active electrode and produces little or no tissue effect. In some designs, the sesquipolar return electrode may be found on the electrode probe-handle structure while on other designs it may be separately located in a non-remote region of the body.

There are a variety of effects that may occur depending upon the electrosurgical mode desired. For instance, there are both high temperature and low temperature desiccation effects when the active electrosurgical probe contact(s) are used to promote tissue desiccation. The resistance of the tissue in contact with the active probe electrode obviously varies with the tissue temperature and water content of the tissue. A low temperature desiccation effect involves heating such that the temperature-time product causes tissue necrosis with little immediate denaturation or discoloration of the tissue. A high temperature desiccation includes heating tissue near the conducting probe contact to approach or slightly exceed 100° C. In the low temperature variation of this procedure, there is a transient decrease in local tissue impedance with little drying of tissue. But in the high temperature variation, there are significant increases in local tissue impedance and also significant in local tissue desiccation.

In the ablation mode, the electrosurgical energy density delivered largely causes the tissue near the probe contact to vaporize. The temperature at the electrode/tissue interface is increased significantly past the point of steam formation. The effect of electrical resistance varies during a specific radio frequency (RF) cycle and although there is sparking, carbonization is not usually significant and the effects of the device are relatively rapid.

Electrosurgical ablation and cutting produce an effect where a thin layer of tissue is vaporized (cutting) or where a larger section of tissue is vaporized (ablation). The line between "cutting" and "ablation" is not always clear.

In the procedure specified below as the invention, a preferable procedure for this invention is via the operation of electrosurgical probes operated in cutting, ablation, or desiccation mode. Herein, when I refer to the term "volume change" or "volume modification" when referring to the material in the corneal mass, I mean the corneal mass is either necrosed, desiccated, or ablated.

It is quite rare that the current flow through the device is DC. The current is typically a very high frequency alternating current, typically in the range of 500 KHz or more.

Additionally, the RF energy is often delivered in a pulsed or in a more continuous, non-pulsed operation depending on the exact effects desired. Some residual heating will take place no matter which course is taken.

With this lengthy background in place, please refer to FIGS. 3A through 3D. This series of figures shows, in schematic fashion, one procedure for treating hyperopia (farsightedness), myopia, or astigmatism. This schematic procedure shows features which may be common to all of the processes of this invention. Generically, the procedure includes the step of producing one or more incisions, often towards the periphery of the cornea. These incisions penetrate Bowman's layer in the anterior surface of the cornea and extend down into, as defined above, "the corneal mass or corneal volume." I also contemplate that the electrosurgical probe may be inserted into the corneal volume without penetration of the anterior surface cornea, e.g., by access through a partial depth incision made in the sclera next to the cornea. In any event, if an anterior access partial depth incision is contemplated, an optional step at this point may be the insertion of a non-electrosurgical lamellar separator to separate the various stroma lamellae within the cornea at the depth of the entry incision. This allows the subsequent step of inserting the electrosurgical probe to take place with greater ease. The probe itself may serve the function of intralamellar separator, if so desired. The electrosurgical probe is introduced into the stromal lamellar cavity so produced. Depending upon the design of the inserted electrosurgical probe and on the refractive effect desired, the probe is moved inside the intralamellar space previously formed and activated to desiccate or ablate specific geometric regions of the cornea. Desirably, after the completion of the corneal volume ablation or desiccation step, the curvature of the corneal surface is then measured. The procedure may be repeated if insufficient correction has occurred. If needed, Bowman's layer and a small amount of underlying stromal tissue may be lightly cut on the anterior surface adjacent to or above the site of the volume reduction to allow the anterior corneal surface to change.

Returning to the specifics of FIGS. 3A to 3D, FIG. 3A shows an eye (100) having a pupil (102) and a cornea (104). In the outer radius of cornea (104) is found two small partial depth incisions (106) which have been cut through Bowman's layer into the corneal mass as shown in FIGS. 1 and 2. These incisions may be cut radially or circumferentially and are shown for discussion purposes to be radial.

Figure 3A:
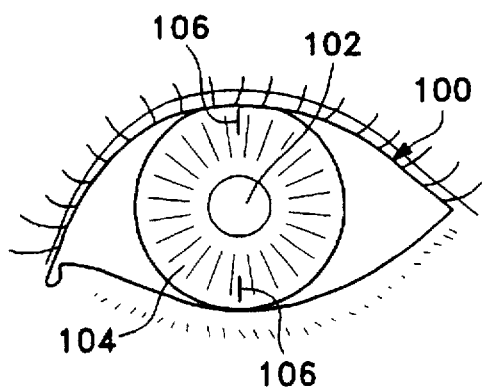
FIGS. 3A to 3E show a schematic process for treatment of hyperopia using the procedure of this invention.
Figure 3B:
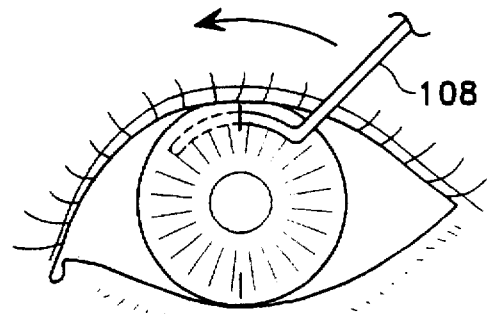

It should be understood, however, that although two access partial depth incisions (106) have been portrayed in FIG. 3A, the number of such access sites (106) is not important. If a semi-circular lamellar separator (108) as shown in FIG. 3B is used, then the number of access sites (106) may be desirably two in number. If lamellar separators of shorter arc segments are used, more numerous slits may be desired. If a nearly circular lamellar separator or electrosurgical probe is used, a single access site (106) may be sufficient.

Figure 3C:
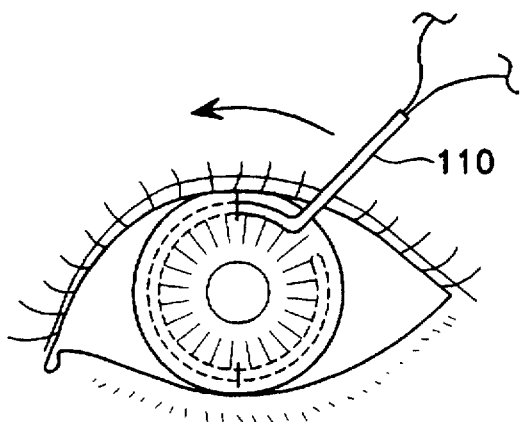

FIG. 3B shows the introduction of the optional dissector blade or lamellar separator (108) to separate the lamella found in the cornea. The separator (108) is rotated until a circular channel is made in the corneal periphery, and is rotated back out of the eye. A similar procedure takes place on the other access site as shown in FIGS. 3A and 3B. FIG. 3C shows the insertion of an electrosurgical probe into the route formed in the intrastromal region shown in FIG. 3B. The probe may be energized following complete insertion or may be energized in a stop, move and activate mode. The step of removing and/or shrinking tissue is continued until sufficient tissue has been ablated or desiccated to achieve the desired refractive effects.

Figure 3D:
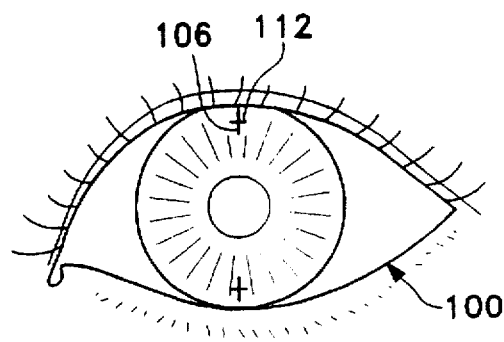
Figure 3E:
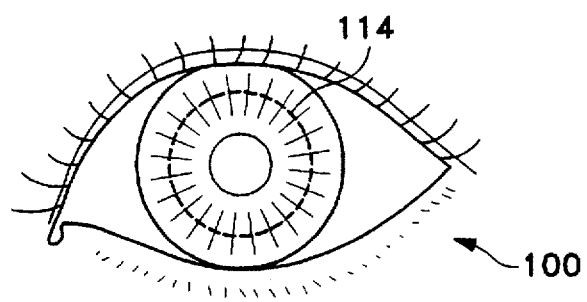

FIG. 3D shows the eye (100) after completion of the ablation procedure. It may be desirable to place a small stitch (112) in any access site (106) in the cornea to ensure healing of the access site and minimize the potential for infection. FIG. 3E shows the eye (100) following relief cuts (114) that may be necessary in some instances to allow the anterior corneal surface to more closely conform to the underlying corneal tissue removal (volume change) thereby allowing for greater change in anterior corneal curvature. These relief cuts may be circumferential as shown or they may be radial depending on the desired refractive effect. Further, the relief cuts may be continuous or may be interrupted as shown. In any case, these cuts will be shallow cuts such that they penetrate Bowman's layer and possibly a portion of the underlying corneal stroma.

The above-description generally indicates the method of the present invention. Specific probe configurations and method of treatment will be described in the Examples below.

It should be apparent from the description above, that the step of desiccating, necrosing or ablating the tissue from within the corneal mass lessens the volume of that mass in specific regions of the cornea. Consequently, the anterior sections of the cornea will become flatter or steeper and will alleviate the improper previous refraction of light. Some of the possible changes in corneal thickness and their relationship to the radius of curvature of the central corneal surface are described in *Jose Barraquer: Father of Modern Refractive Keratoplasty*, in Refractive and Corneal Surgery, Vol. 5, May/June 1989, pages 177–193, which is hereby incorporated by reference in its entirety. This paper describes the so-called "Law of Thickness" which indicates that when corneal volume is reduced in the periphery, central corneal steepening occurs and when a volume of tissue is removed in the center, central corneal flattening occurs. The inventive electrosurgical method and devices aim to reduce corneal volume in controlled geometric areas of the corneal stroma to achieve refractive correction.

Figure 4A:
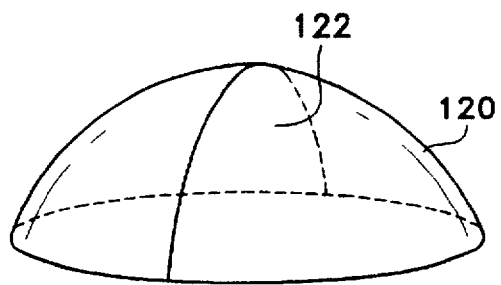
FIGS. 4A to 4D show schematic diagrams of astigmatic and normal eyes.
Figure 4B:
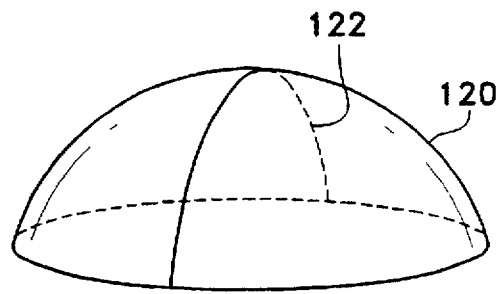
Figure 4C:
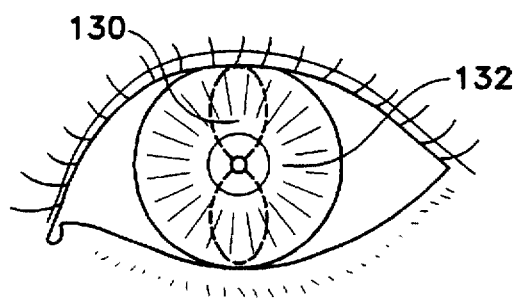
Figure 4D:
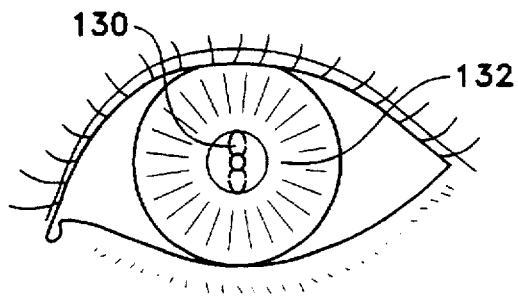

The method and devices of the present invention may also be useful in the treatment of astigmatism. Astigmatism occurs, generally, when the curvature of the anterior surface of the cornea is not regular as one passes about the meridians on the anterior surface of the cornea resulting in a steep and flat axis (the astigmatic axis). FIG. 4A and 4B are schematic perspective views that show an astigmatic and normal eye, respectively. In an astigmatic eye, two axes are generally identified, corresponding to the steepest (120) and flattest (122) axis of curvature. The steepest axis is also known as the axis of astigmatism (120). To correct astigmatism using this invention, one must flatten the curvature of the astigmatic axis such that the cornea becomes reasonably symmetrical and more spherical. FIG. 4B shows a normal eye, that is, one in which the curvature of all axes are the same. FIGS. 4C and 4D show schematic topographical curvature maps of an astigmatic and of a non-astigmatic eye, respectively. In FIG. 4C, region 130 is the steep region where as region 132 is flatter.

Other configurations of access sites and controlled removal of corneal tissue are apparent. These will be discussed for particular applications in the Examples below. Further, it should be apparent to one appreciating the design of such electrosurgical RF probes, that the shape need not be nearly circular. It may be, much in the same way as were the lamellar separators (108) in FIG. 3B, that the probes have lesser arc length or are straight for alleviating hyperopia. In fact, for treating hyperopia or other maladies, the probe may be of any convenient shape designed to ablate the tissue at hand. Such shapes will be discussed in more detail below. Further it may be noted that the handles of the probes may be straight or bent. A bent handle may allow greater facility of use within the small confines found behind an access site, as shown in the above drawings. Additionally, the procedures and devices of the present invention may be useful in the treatment of more than one indication, for example myopia and astigmatism or hyperopia and astigmatism.

FIGS. 5–11 A and B show top (A) and side (B) views of circular electrosurgical probes suitable for use in the schematic procedure described above. FIGS. 5A and B show a circular RF electrosurgical probe with two active sites that operate in monopolar or sesquipolar modes. The probe (200) includes a shaft (202) and two active sites (204), each active site having an arc of less than about 180°, preferably less than about 90°. The single source of RF energy (206) is fed in through the insulator (208) making up the probe (200). FIGS. 6A and B show a circular RF electrosurgical probe (210) with a single active site (212) at the tip. Again, the single source of RF energy (214) is fed in through the insulator making up the probe. FIG. 7A and 7B show a circular RF electrosurgical probe (220) with a single active site (222) extending the length of the circular portion of the probe. Once more, the single source of RF energy (224) is fed in through the insulator (226) making up the probe. FIGS. 8A and B show a circular RF electrosurgical probe (230) with two active sites (232) near the tip of the probe that operate in bipolar fashion. Two sources of RF energy (234 and 236) are fed in through the insulator (238) making up the probe. FIGS. 9A and B show a circular RF electrosurgical probe (240) with a single active site (242) near the tip, the active site shown in FIG. 9A to be on the top part of the probe. A single source of RF energy (244) is fed in through the insulator (246). FIGS. 10A and B and 11A and show other circular RF electrosurgical probes (250 and 260 respectively) with single active sites (252 and 262 respectively) near the tips of the probes. A single source of RF energy (254 and 264) is fed in through each probe. FIG. 10B shows the active site (252) to be located at the tip but exposed on one side and FIG. 11B shows the active site (262) to be located at the tip but insulated on the top and thus exposed on one side only. Both probes depicted in FIGS. 10 A and B and 11 A and B are designed to contact tissue in either the forward or retracting direction to the active site on the probe, the retracting direction.

FIG. 12–19 A and B show top (A) and side (B) views of straight electrosurgical probes suitable for use in the schematic procedure described above. FIGS. 12A and B shows a straight RF surgical probe (300) with a single active site (302) extending along the length of the probe. A single source of RF energy (304) is fed through the probe. FIGS. 13A and B show a straight RF electrosurgical probe (310) with two active sites (312) extending along the length of the probe that operate in bipolar fashion. Two sources of RF energy (314 and 316) are fed in through the insulator (318) making up the probe. FIGS. 13–19 A and B show other straight RF electrosurgical probes with single active sites near the tips of the probes. A single source of RF energy is fed in through each probe. FIGS. 14 A and B show the active site (322) to be located near the tip of the probe (320) and on top of the probe such that the active site is raised and pointed in the retracting direction of the probe. FIGS. 15A and B show the active site (332) similarly located near the tip of the probe. The end of the probe is raised and the active site (332) is located on the raised part of the tip pointing backwards, the active site being exposed on two sides. FIGS. 16A and B similarly show the active site (342) raised at the end of the probe pointing backwards (340), but the active site is imbedded in the insulating curve of the probe, thereby exposing the active site on one side only. FIGS. 17A and B show the active site (352) at the tip of a straight probe (350), the active site being exposed on one side on the tip portion alone. FIGS. 18A and B show the active site (362) near the end of a straight probe (360). The probe is broadened at the active site. FIGS. 19A and B again show a straight RF electrosurgical probe (370) with a curved tip, with the active site (372) again raised and pointing backwards and slightly upwards the active site being exposed on one side on the tip portion alone. However, in this embodiment active site is angled such that a portion (374) of the active site (372) extends beyond the curved tip. In this design, the ablation or desiccation takes place either as the device is pushed forward or as it is pulled backwards, or retracted from the lamellar separation channel. Upon exposure to tissue and electrode activation, the active site will vaporize or desiccate the tissue. It may be desirable to provide a second lamellar channel to allow for the for the relief of gases produced by the probe when used in the ablation mode or to incorporate grooves in the probe portions that insert into the tissue to allow the escape of gases so produced.

Figure 20A:
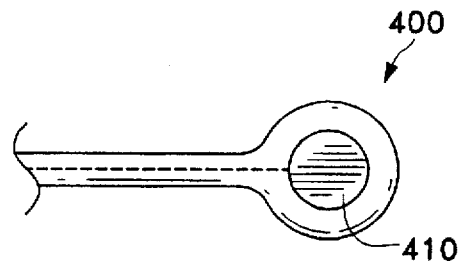
FIGS. 20 A and B and 21 A, B and C show top (A and C) and side (B) views of inventive disc and washer RF electrosurgical probes.
Figure 20B:
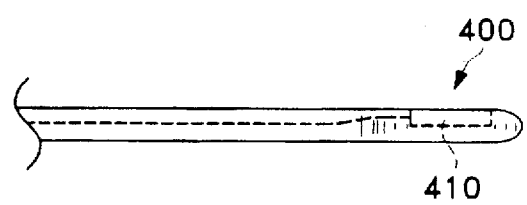
Figure 21A:
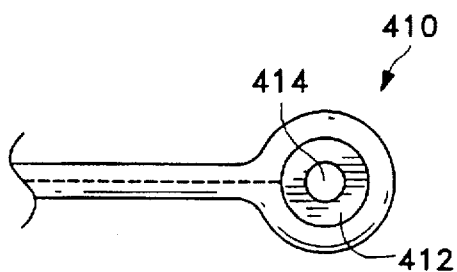
Figure 21B:
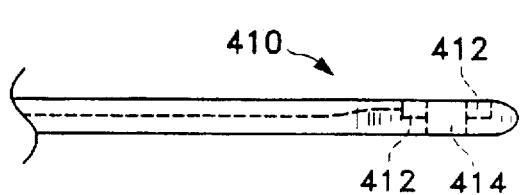
Figure 21C:
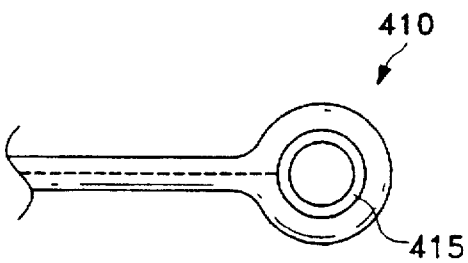

FIGS. 20 and 21 A and B show top (A) and side (B) view of RF electrosurgical disc and washer probes (400 and 410 respectively). A single RF energy source is fed through each probe. The disc probe (400) is a circular probe with a circular active site (410). The washer probe (410) is a circular probe with a circular active site (412) with a hollow middle (414). Each of these probes may have a flat surface as shown in FIGS. 20A and 21A or may be curved to conform to the curvature of the cornea. The disc probe may have a wire loop surface (415) as shown in FIG. 21C.

The above described probes are useful in the particular examples discussed below. The Examples are illustrative only and are not intended to limit the scope of the invention. For the probes that have only one conducting lead to deliver RF energy (i.e. monopolar or sesquipolar) a return electrode is necessary. In some instances this may be placed remotely on the body. In other cases, the use of a sesquipolar return electrode may be desired using a return electrode that is placed onto the sclera or translimbal area of the cornea.

Figure 22:
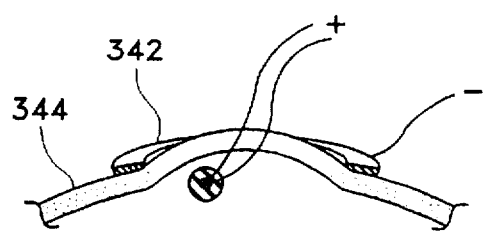
FIG. 22 shows a desired return electrode for the sesquipolar probes of the other Figures.

FIG. 22 shows a desirable manner for placing a sesquipolar return electrode on the exterior of the cornea, or onto the sclera (344). This return electrode may simply rest on the cornea or sclera as shown or may be held in place by a vacuum attachment cavity built into the electrode. As noted above, the area of this return electrode (342) where it contacts the eye is without much exception constant. Because of its significantly higher area as compared to the active tissue contacting electrodes described above, the tendency for the return electrode (342) to heat to a significant degree is minimized. The sesquipolar electrosurgical system described above is an embodiment of this invention that can enhance the safety of this ophthalmologic operation.

The following Examples are intended to describe particular embodiment of the invention but are in no way intended to limit the invention in any manner.

EXAMPLES

Example 1

The Correction of Astigmatism

Figure 23A:
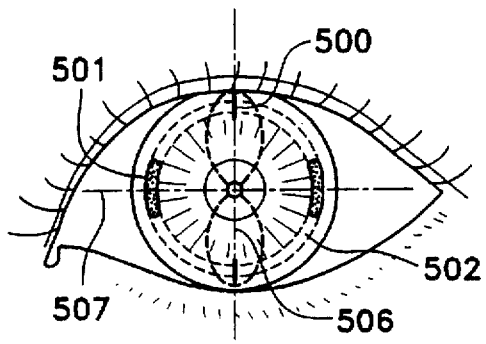
FIGS. 23 A–G are schematic diagrams showing top views of eyes wherein various processes for electrosurgically altering corneal curvature have been carried out.
Figure 23B:
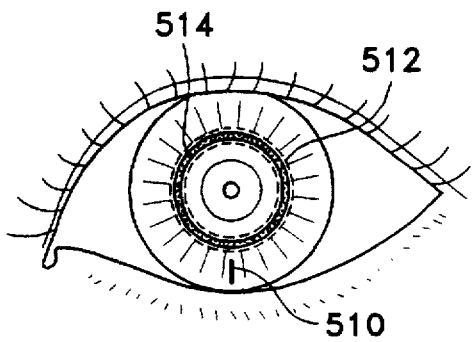
Figure 23C:
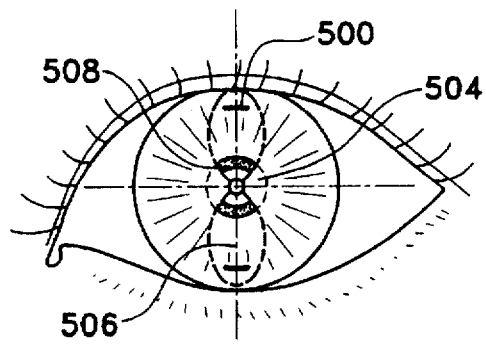

In order to correct the astigmatic eye shown in FIGS. 4A and 4C such that it becomes more similar to that shown in FIGS. 4B and 4D, a process similar to that described above with regard to FIGS. 3A–3D is carried out. As shown in FIGS. 23A and 23C, radial or circumferential partial depth incisions (500) are made in the periphery of the cornea. A lamellar separator is inserted to create a zone of separated lamellae (502) and (504) for the insertion of the electrical probe.

Two different approaches are possible to correct the astigmatic eye. In the first approach shown in FIG. 23C the radial partial depth incisions and radial zone of separated lamellae will be formed beneath the astigmatic axis (506). Following separation of the lamellar tissue, one of the straight RF probes shown in FIGS. 14–19 A and B is inserted through the partial depth incision (500). The probe is then activated to change the paracentral corneal volume (508), that is the volume near the center of the cornea, by ablation of the tissue under the figure-8-shaped astigmatism shown in FIG. 23A and 23C. The choice of RF probe design is dependent on the amount of tissue to be ablated. Once ablation is completed, the probe is withdrawn. Relief cuts on the anterior cornea may be necessary as described above to allow the surface of the cornea to conform to the underlying tissue removal. In this way, the steep astigmatic axis is flattened such that the cornea becomes reasonable symmetrical and spherical.

A second approach to the treatment of an astigmatic eye is to steepen the flat astigmatic axis as shown in FIG. 23A. In this approach, the lamellar separation zone will be formed in the periphery of the cornea (502). The partial depth incision (500) is placed in the corneal periphery, beneath the astigmatic axis. Following separation of the lamellar tissue, one of the circular RF probes shown in FIGS. 5, 6, 8, 9, 10, and 11 A and B, probes (200), (210), (220), (230), (240), (250) and (260) respectively, is inserted through the partial depth incision (500). The probe is then activated to change the volume by desiccation (probes (200), (210), (230), (240), (250) or (260)) or by ablation (probes (210), (240), (250), or (260)) of the tissue (501) under the flat axis of astigmatism axis (507) as shown in FIG. 23A. Thus some probe configurations can be used either in the ablate or in the desiccation mode. Probe (200) is operated by inserting it into the lamellar tissue, activating it, deactivating it, and then removing it. Probes (210), (230), (240), (250), and (260) are operated by inserting into the lamellar tissue, activating, deactivating, rotating to a second position to be desiccated or ablated, activating, and then removing. Again, the choice of RF probe design is dependent on the amount of tissue to be ablated or desiccated. Once ablation or desiccation is completed, the probe is withdrawn. Relief cuts to the anterior cornea may be necessary as described above to allow the surface of the cornea to conform to the underlying tissue modification. In this way, the flat, astigmatic axis (507) is steepened such that the cornea becomes reasonable symmetrical and spherical.

Example 2
The Correction of Hyperopia

Figure 23D:
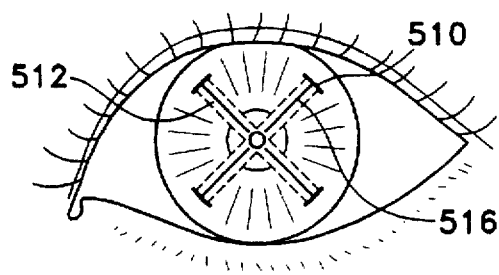
Figure 23E:
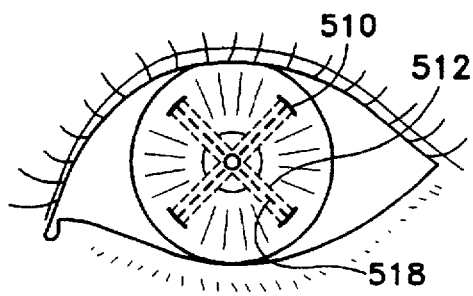

In order to correct hyperopia a process similar to that described above with regard to FIGS. 3A–3D is carried out. As shown in FIGS. 23B, 23D and 23E, radial or circumferential partial depth incisions (510) are made in the periphery of the cornea. A lamellar separator is inserted to create a lamellar pathway (512) for the insertion of the electrical probe.

Two different approaches are possible to correct the hyperopic eye. In the first approach, shown in FIG. 23B partial depth incisions (510) are made in the peripheral cornea and a circumferential lamellar separation zone (512) will be formed beneath the corneal surface. Following separation of the lamellar tissue, one of the circular RF probes shown in FIGS. 6–11 A and B is inserted through the partial depth incision (512). The probe is then activated to change the volume by ablation or desiccation of the tissue (514) in the channel. The choice of RF probe design is dependent on the amount of tissue to be ablated or desiccated. Probes (210), (220), (230), (240), (250) and (260) will allow for desiccation of the channel. Probe (220) is operated by inserting it into the lamellar tissue, activating it, deactivating it, and then removing it. The other probes are operated by inserting them into the lamellar tissue, activating, deactivating, rotating to a second position to be ablated, activating, deactivating and repeating this process until the entire channel is desiccated, and then removing it. Probes (210), (240), (250) and (260) will allow for ablation of the channel. The probes are operated by insertion into the lamellar tissue, activation, deactivation, rotation to a second position to be ablated, activation, and repeating until the entire channel is ablated, followed by removal of the probe. Probes (250) and (260) can also be operated by complete insertion into the lamellar tissue, activation, deactivation, pulling partially back out of the tissue to a second position to be ablated, activation, deactivation and repetition of this process until the entire channel is ablated, followed by removal of the probe. Again, relief cuts in the anterior of the cornea may be necessary as described above to allow the surface of the cornea to conform to the underlying tissue removal. In this way, the central corneal surface is steepened such that the cornea curvature is improved.

A second approach to the treatment of a hyperopic eye is to use a straight RF probe. In this second approach 2 or more partial depth incisions (510) are made in the periphery and 2 or more radial lamellar separation zones are formed as shown in FIGS. 23D and 23E. Following separation of the lamellar tissue, one of the straight RF probes shown in FIGS. 12–19 A and B is inserted through each partial depth incision (510) in the lamellar separation zones (512) and (514). The probe is then activated to change the volume by ablation or desiccation of the tissue in the channel. The choice of RF probe design is dependent on the amount of tissue to be ablated or desiccated. Probes (300), (310), (320), (330), (340), (350), (360) and (370) will allow for desiccation of the channel. Probes (300) and (310) are operated by insertion into the lamellar tissue, activation, deactivation, and then removal. Probes (320), (330), (340), (350), (360) and (370) are operated by inserting into the lamellar tissue, activating, deactivating, moving to a second position to be ablated, activating, deactivating and repeating this process until enough of the channel is desiccated, and then removing the probe. In this way the tissue desiccated can either form a continuous path (516) or can be interrupted points along the radial lamellar separation channel (518). Probes (320)–(370) will allow for ablation of corneal volume inside the radial lamellar separation channel. Probes (320), (340), (350), (360) and (370) are operated by insertion into the lamellar tissue, activation, deactivation, moving it further into the tissue to a second position to be ablated, activation, and repeating until the entire channel is ablated, and then removal. The same probes can also be operated by complete insertion into the lamellar separation channel, activation, deactivation, pulling back out of the tissue channel to a second position to be ablated, activation, deactivation and repetition of the process until the enough of the channel is ablated, followed by removal of the probe. Again, relief cuts may be necessary in the anterior cornea as described above to allow the surface of the cornea to conform to the underlying tissue removal. In this way, the corneal surface is steepened centrally such that the corneal curvature is improved.

Example 3
The Correction of Myopia

Figure 23F:
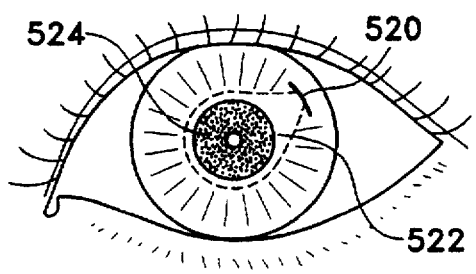
Figure 23G:
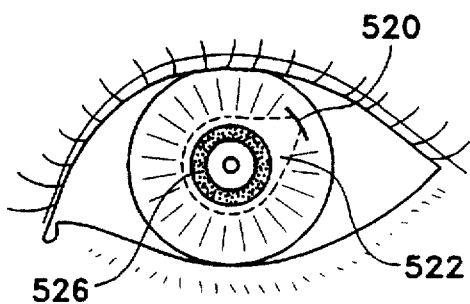

In order to correct myopia the process similar to that described above with regard to FIGS. 3A–3D is carried out. As shown in FIGS. 23F and 23G, radial or circumferential partial depth incisions (520) are made in the periphery of the cornea. A lamellar separator is inserted to create a radial lamellar separation channel (522) toward the center of the pupil for the insertion of the electrical probe.

For correction of myopia, the lamellar path (522) will be formed under or near the central or paracentral portion of the cornea. Following separation of the lamellar tissue, one of the straight RF probes shown in FIGS. 14–19 A and B or the disc or washer probes shown in FIGS. 20–21 A and B is inserted through the peripheral partial depth incision (520) into the lamellar separation channel (522). The probe is then activated to change the volume by ablation of the tissue in the channel, the volume change (524) resulting from the use of the disc-shaped probe (400) is shown in FIG. 23F and volume change (526) resulting from the use of the washer-shaped probe (410) is shown in FIG. 23G. The choice of RF probe design is dependent on the amount of tissue to be ablated. Probes (320)–(370) will allow for ablation of the channel. The probes are operated by insertion into the lamellar tissue, activation, deactivation, advancing the probe into the channel to a second position to be ablated, activation, deactivation, repeating the process until the entire channel is ablated, and then the probe is removed. The probes can also be operated by complete insertion into the lamellar separation channel, activation, deactivation, pulling out of the channel to a second position to be ablated, activation, deactivation and repeating the process until the entire channel is ablated, and then the process is removed. Probes (400) and (410) are operated by insertion into the lamellar separation channel (522), activation, deactivation and removal from the channel. Again, relief cuts in the anterior cornea may be necessary as described above to allow the surface of the cornea to conform to the underlying tissue removal. In this way, the corneal surface in the central corneal area is flattened such that the corneal curvature is improved.

The foregoing examples of procedures and devices according to the present invention are only representative and are not meant to be in any manner limiting. Other embodiments, areas of application, methods of use of the present invention, within the scope of the claims appended hereto, will be evident to those skilled in this art. Other embodiments of the procedures without the scope of the claims but within the spirit of invention described herein are considered to be equivalent to those procedures and devices claimed.

I claim as my invention:

1. An electrosurgical probe comprising a support end and a substantially hook-shaped contact end where said contact end comprises at least one active tissue contacting site disposed on a surface of said contact end, the plane of the contact end is substantially coplanar with corneal lamellae when the probe is introduced into a corneal mass, an area of the at least one active site is substantially smaller than an area of the contact end surface on which the at least one active site is disposed, and the active site is in electrical connection with an insulated conductor residing within said contact end and extending to the support end.

2. The electrosurgical probe of claim 1, said probe comprising two active tissue contacting sites, the active sites being in electrical connection with a single insulated conductor residing within said contact end and extending to the support end.

3. The electrosurgical probe of claim 1, said probe comprising a single active tissue contacting site, said active site being located in a tip of the contact end.

4. The electrosurgical probe of claim 1, said probe comprising a single active tissue contacting site wherein the active site comprises an arc of less than about 350°.

5. The electrosurgical probe of claim 1, said probe comprising two active tissue contacting sites that are each in electrical connection with their own separate conductor residing within said contact end and extending to the support end.

6. The electrosurgical probe of claim 1, said probe comprising a single active tissue contacting site located near a tip of the contact end on a top portion of the probe.

7. The electrosurgical probe of claim 1, said probe comprising a single active tissue contacting site located near a tip of the contact end and raised and pointed in a retracting direction of the probe.

8. An electrosurgical probe comprising a support end and a contact end where said contact end comprises at least one active tissue contacting site, the height of the contact end is generally less than the width of the contact end, a substantial portion of the at least one active site is disposed on a major surface of the contact end, the at least one active site is in electrical connection with a conductor residing within said contact end and extending to the support end, the conductor is adapted to be coupled to an electrical signal source, and the probe modifies a corneal mass when the probe is introduced into the corneal mass and the at least one active site is energized by the signal source to thereby alter the anterior corneal surface and correct refractive error.

9. The electrosurgical probe of claim 8, said probe comprising a single active tissue contacting site, said active site extending along a length of the contact end and located on a top portion of the probe.

10. The electrosurgical probe of claim 8, said probe comprising a two active tissue contacting sites that are each in electrical connection with their own separate conductor residing within said contact end and extending to the support end.

11. The electrosurgical probe of claim 8, said probe comprising a single active tissue contacting site located near a tip of the contact end located on a top portion of the probe.

12. The electrosurgical probe of claim 8, wherein a single active tissue contacting site is located near a tip of the contact end and raised and pointed in a retracting direction of the probe.

13. The electrosurgical probe of claim 8, wherein said contact end is broadened and wherein a single active tissue contacting site is located within the broadened contact end.

14. The electrosurgical probe of claim 8 further comprising a washer-shaped single active tissue contacting site at a distal end of the contact end.

15. The electrosurgical probe of claim 8 further comprising a disc-shaped single active tissue contacting site at a distal end of the contact end.

16. The electrosurgical probe of claim 15 wherein a wire loop forms the surface of the disc-shaped active site.

17. A sesquipolar electrosurgical kit for electrosurgically altering the shape of the corneal surface of the eye, said kit comprising in packaged combination:

(a) an electrosurgical probe comprising a support end and a substantially hook-shaped contact end, wherein the plane of the contact end is substantially coplanar with corneal lamellae when the probe is introduced into a corneal mass, and said contact end comprises at least one active tissue contacting site; and (b) a sesquipolar return electrode that is adapted for positioning on or near the eye.

18. A sesquipolar electrosurgical kit for electrosurgically altering the shape of the corneal surface of the eye, said kit comprising in packaged combination:

(a) an electrosurgical probe comprising a support end and a contact end wherein said contact end comprises at least one active tissue contacting site, the height of the contact end is generally less than the width of the contact end, and a substantial portion of the at least one active site is disposed on a major surface of the contact end; and (b) a sesquipolar electrode that is adapted for positioning on or near the eye.

19. The electrosurgical probe of claim 1, wherein said substantially hook-shaped contact end has an open, substantially circular shape.

20. The electrosurgical probe of claim 1, wherein the contact end is substantially flat.

21. The electrosurgical probe of claim 8, wherein the area of the at least one active site is substantially smaller than the area of the major surface on which the at least one active site is disposed.

22. A procedure for altering the shape of the anterior corneal surface of an eye having a corneal mass posterior to the anterior corneal surface, wherein the corneal mass has a volume, the procedure comprising the steps of:

initiating at least one access site into the corneal mass posterior to Bowman's layer, separating lamella of the corneal mass to create a separation zone for receiving an electrosurgical probe, wherein not more than one lamellar separation is performed to create each separation zone, introducing through said at least one access site the electrosurgical probe into the separation zone, and energizing said electrosurgical probe to modify the volume of the corneal mass adjacent to said electrosurgical probe.

23. The procedure of claim 22 where the energizing step comprises the step of modifying the corneal mass by ablation.

24. The procedure of claim 22 where the energizing step comprises the step of modifying the corneal mass by desiccation.

25. The procedure of claim 22 where the energizing step comprises the step of modifying the corneal mass with a bipolar RF electrode.

26. The procedure of claim 22 where the energizing step comprises the step of modifying the corneal mass with a monopolar RF electrode.

27. The procedure of claim 22 where the energizing step comprises the step of modifying the corneal mass with an electrosurgical RF electrode in a sesquipolar configuration.

28. The procedure of claim 22 where the energizing step comprises the step of modifying the corneal mass with an electrosurgical probe in the form of a substantially hook-shaped probe.

29. The procedure of claim 22 where the energizing step comprises the step of modifying the corneal mass with an electrosurgical probe that forms a probe of less than about 350°.

30. The procedure of claim 22 where the energizing step comprises the step of modifying the volume of the corneal mass to correct hyperopia.

31. The procedure of claim 24 where the energizing step comprises the step of modifying the volume of the corneal mass to correct hyperopia or astigmatism.

32. The procedure of claim 27 where the energizing step comprises the step of modifying the volume of the corneal mass to correct hyperopia, myopia or astigmatism.

33. The procedure of claim 22 additionally comprising the step of placing a relief cut in at least a portion of Bowman's layer.

34. The procedure of claim 22 where the energizing step comprises the step of modifying the volume of the corneal mass to alleviate astigmatism.

35. The procedure of claim 22 where the energizing step comprises the step of modifying the volume of the corneal mass to correct myopia.

36. The procedure of claim 35 where the energizing step comprises the step of modifying the volume of the corneal mass at or near the center of the cornea.

* * * * *